United States Patent [19]

Holtman

[11] Patent Number: 4,590,114

[45] Date of Patent: May 20, 1986

[54] STABILIZED ABSORBENT STRUCTURE CONTAINING THERMOPLASTIC FIBERS

[75] Inventor: Dennis C. Holtman, Flemington, N.J.

[73] Assignee: Personal Products Company, Milltown, N.J.

[21] Appl. No.: 601,754

[22] Filed: Apr. 18, 1984

[51] Int. Cl.[4] .............................................. B32B 5/14
[52] U.S. Cl. ..................................... 428/171; 156/62.2; 156/209; 156/296; 428/156; 428/198; 428/221; 428/280; 428/296; 428/326; 428/360; 604/370
[58] Field of Search ............... 428/198, 288, 296, 360, 428/156, 172, 171, 280, 326, 221; 162/10, 13, 142, 150, 146; 156/62.2, 209, 296; 604/370

[56] References Cited

U.S. PATENT DOCUMENTS

| | | | |
|---|---|---|---|
| 2,757,148 | 7/1956 | Heritage | 162/10 |
| 4,047,531 | 9/1977 | Karami | 604/374 |
| 4,082,886 | 4/1978 | Butterworth et al. | 428/296 |
| 4,392,861 | 7/1983 | Butterworth et al. | 428/296 |

FOREIGN PATENT DOCUMENTS 572962  9/1975  United Kingdom ............... 162/146

Primary Examiner—James J. Bell
Attorney, Agent, or Firm—Martha A. Michaels

[57] ABSTRACT

A batt including a major percent of thermo-mechanical wood pulp fibers is stabilized by the inclusion of a minor percent of thermoplastic fibers, which latter fibers are heat fused to one another and to the thermo-mechanical wood pulp fibers at fiber intersections to provide a supporting network which inhibits collapse and agglomeration of the thermo-mechanical wood pulp fibers.

21 Claims, 6 Drawing Figures

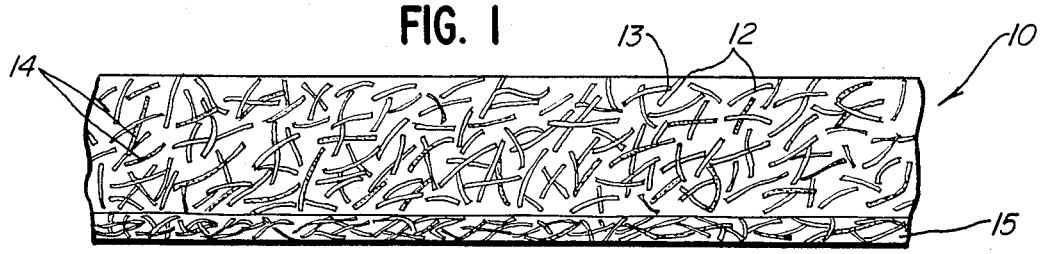
FIG. 1
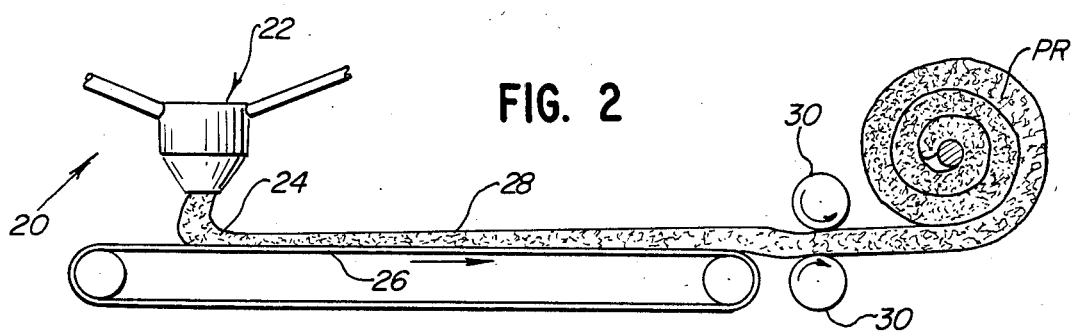
FIG. 2
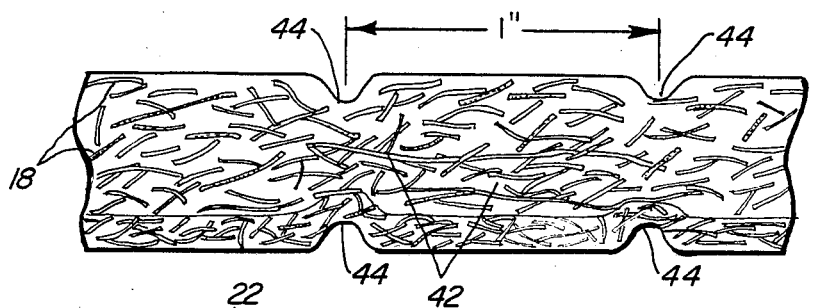
FIG. 3
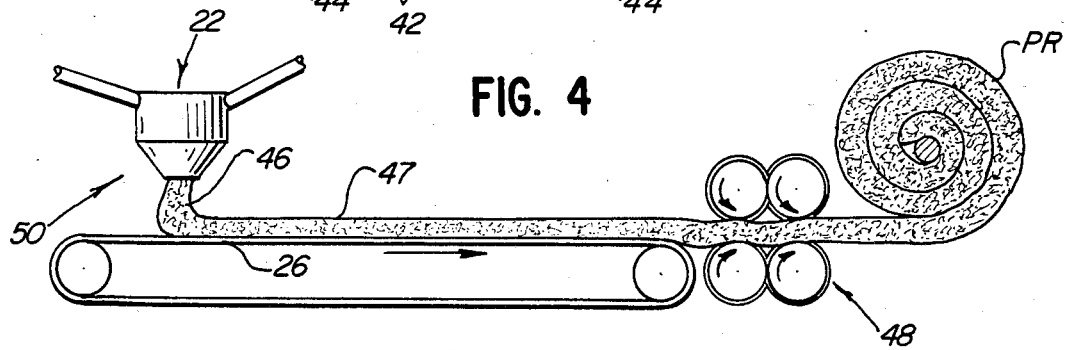
FIG. 4
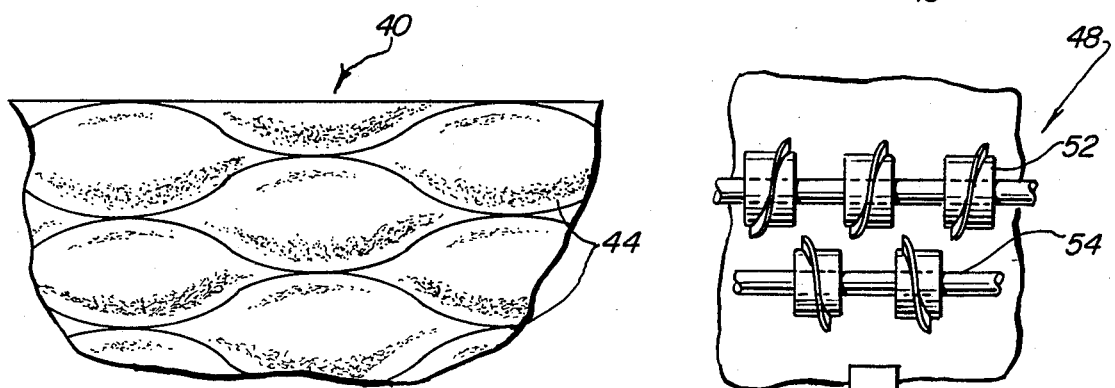
FIG. 5
FIG. 6

STABILIZED ABSORBENT STRUCTURE CONTAINING THERMOPLASTIC FIBERS

TECHNICAL FIELD

This invention relates to an absorbent structure for use in diapers, sanitary napkins, and the like. More particularly, the invention relates to an improved absorbent structure including non-delignified wood pulp fibers.

BACKGROUND OF THE INVENTION

For many years it has been well known to employ natural wood pulp fibers in the manufacture of the absorbent pad or core of disposable products such as diapers, sanitary napkins, surgical dressings, and the like. In the most general sense, there are but two basic processes, chemical and mechanical, for producing pulp fibers from natural wood. The characteristics of the pulp produced by the two basic processes differ considerably and, depending upon the intended final use to be made thereof, each has certain advantages and disadvantages.

In chemical wood pulping, there is a total or partial digestion and removal of the hydrophobic constituents of the wood, such as, lignin, carbohydrates and other nonligneous materials. The yield of chemical pulp is predictably low and expensive, on the order of around 50%.

Mechanical pulping processes are more cost efficient, producing yields on the order of 90% and higher. Understandably, mechanical wood pulp, sometimes known as refiner pulp, is substantially hydrophobic due to the presence of lignin and other non-absorbing materials.

More recently, there has been increasing use of wood pulp produced by thermo-mechanical processes. Thermo-mechanical pulp (TMP) is essentially mechanical pulp, but has modified qualities because of an additional heating step. The thermomechanical process involves a step of first heating the wood chips to about 270° F., usually with steam, to soften them for further mechanical processing. This heating stage tends to soften but not remove the lignin and also to loosen the individual wood fibers to ease actual defibration. Thermo-mechanical pulp thus has somewhat longer fibers than plain refiner pulp and produces structures of higher loft and greater flexibility.

Non-delignified wood pulp fibers, such as the thermo-mechanically produced wood pulp fibers, refiner produced wood pulp fibers, or the like, have become quite important in the last few years. These wood pulp fibers, also referred to as "high yield" wood pulp fibers, have become increasingly important for several reasons. The processes used to produce the fibers not only utilize more of the raw material than typical chemical processes, but the non-delignified wood pulp processes also reduce the environmental problems caused by chemical processing. Specifically, the "high yield" processes cause considerably less air pollution and water pollution than do the counterpart chemical processes. These various factors and the concomitant economic considerations make the high yield processes, such as the thermomechanical pulp process, very attractive.

Non-delignified wood pulp processes have been known for some time and are usually developed primarily for paper grade wood pulps, newsprint, and the like. These wood pulps have not been well accepted in absorbent type products, such as sanitary napkins, disposable diapers, and the like, primarily because of their relatively poor performance as the absorbent core for such products.

Conventional chemically processed wood pulp fibers have a degree of cohesive strength when placed in an air-laid web structure. Typically chemically processed wood pulp fibers are somewhat collapsed and appear in ribbon-like form. This form permits fiber entanglement during the air-laid web processing and hence results in a web having a degree of cohesiveness and fibrous web integrity.

In contrast, the non-delignified wood pulp fibers are non-collapsed, stiffer and more resilient. Webs formed of these fibers, although possessing a greater potential liquid holding capacity, have poor integrity and hence tend to break apart.

Furthermore, absorbent structures made from non-delignified wood pulp fibers are substantially hydrophobic and not readily wettable. For any absorbent structure to be satisfactory, it is highly desirable for the structure to (1) readily accept liquid, (2) easily transport the liquid from one portion of the structure to another, and (3) hold the liquid accepted.

Various techniques have been developed or suggested for improving the absorbent characteristics of non-delignified wood pulp, such as removing the fines from the wood pulp product or providing various solvent or other chemical treatments to the wood pulp product to both bleach the pulp and improve its absorbency. However, these techniques increase the economics or cost of the wood pulp and, in some instances, increase the pollution problem and, hence, do not take full advantage of the non-delignified wood pulp process.

Development of the use of mechanical wood pulp and thermo-mechanical pulp and some of the problems encountered in such use may best be appreciated by reference to some illustrative prior art examples. In "Mechanical Pulp In Absorbent Qualities", published by The Norwegian Pulp and Paper Institute (Sept., 1973) E. Bohmer et al describe the possible use of plain refiner or thermo-mechanical pulp in place of chemical pulp on a basis of cost, but conclude that it cannot achieve the liquid-holding capacity of chemical pulp. In "Thermo-Mechanical Pulp For Diapers, Other Absorbent Products" (Nov. 1975) Weyerhaeuser Company describes its new thermo-mechanical process for making pulp called Eco-Fluff and some of its potential uses. Among U.S. Pat. No. 4,047,531 teaches a two-layer pad, one of mechanical or thermo-mechanical pulp and the second of thermo-mechanical or chemical pulp; Butterworth, et al U.S. Pat. Nos. 4,081,582 and 4,129,132 teach a two-layer non-woven fibrous material, one layer of wood pulp, the second of thermoplastic synthetic wood pulp fibers with some heat-induced bonding at the interface of the layers; U.S. Pat. No. 4,120,747 teaches an absorbent paper made of thermo-mechanical or chemi-thermo-mechanical pulp; U.S. Pat. No. 4,154,883 teaches a multi-ply wipe or swab including a backing layer of adhesively bonded wood pulp and a second layer of absorbent wood pulp and synthetic wood pulp; and U.S. Pat. No. 4,215,692 teaches an absorbent structure comprising a mixture of mechanical wood pulp (thermo-mechanical or refiner) and peat.

Other techniques for developing absorbent products utilizing non-delignified wood pulps have been suggested. One technique is disclosed in British Pat. No. 1,500,053 and uses fibers of specific measurement; that is, length and diameter. The surface hydrophilicity of the fibers is increased by bleaching and the hydrophilic fibers are air-laid in web form and compressed to a specific density. Bleaching followed by compression substantially increases the wettability of the otherwise hydrophobic structure, but at the same time, reduces the liquid holding capacity of an absorbent structure made from non-delignified wood pulp fibers.

As mentioned above, for any absorbent structure to be satisfactory, it is not only necessary for the structure to hold liquid but also to readily accept liquid and transport it. The liquid holding capacity of the absorbent structure relates to the pore size of the fibrous bed and the wet bending modulus of the fibers. If the pore size (i.e., the spaces surrounding the fibers) is large and the wet bending modulus (i.e., stiffness) of the fibers is high, then the structure will have a relatively high liquid holding capacity but generally does not transport (wick) liquid readily. On the other hand, if the pore size is smaller and the bending modulus relatively low, the structure readily wicks liquid but will have a lower liquid holding capacity.

The fibers from the non-delignified wood pulp process can provide an absorbent structure having a large pore size and a high wet bending modulus of the fibers, however, such absorbent structures do not readily accept liquid, nor will the structure be readily densified or embossed to promote wicking.

As indicated by the cited illustrative references, the numerous efforts in this highly developed art to provide an absorptive structure utilizing cost efficient and desirable thermo-mechanical pulp are beset with difficulties that remain unsolved. These difficulties are partially or completely overcome by the present invention.

SUMMARY OF THE INVENTION

In the broadest sense the invention comprises a single layer absorbent batt made predominantly of thermo-mechanical pulp (TMP). The batt is formed by blending a major percentage of the non-delignified TMP fibers with a minor percentage of thermoplastic fibers, which may take the form of synthetic wood pulp fibers (SWP), or staple length thermoplastic fibers, or a combination of SWP and staple length thermoplastic fibers. The TMP and thermoplastic fibers are first thoroughly mixed to provide a substantially homogeneous blend so that thermoplastic fibers are intermixed everywhere throughout the basically TMP web. Heat is applied to the substantially homogeneous web of a degree sufficient to at least partially melt the thermoplastic fibers, but leave physically unaffected the non-delignified TMP fibers. Upon cooling, the solidified portions of the thermoplastic fibers provide bond sites which secure the TMP fibers to one another at points of individual fiber contact to form a stabilizing network which supports the batt to maintain interstitial spacing and resist agglomeration and wet collapse of the TMP fibers.

In another form of the invention, the substantially homogeneous batt described may additionally include a densified layer of chemical pulp at one face thereof to provide a wicking layer.

In both forms of the invention already described, a majority of the fibers are TMP fibers, which are typically inexpensive paper making fibers having lengths on the order of ¼ inch or less. To achieve the purposes of the present invention, at least about 5% of the fibers should be thermoplastic fibers, but the amount of thermoplastic fibers may vary from about 5% to about 25%.

Variations of each of the two embodiments described contemplate the application of heat embossing on one or both faces of the batt to provide locally densified areas for achieving a further stabilized structure.

In the embodiment of the invention which comprises a substantially homogeneous blend of TMP and staple or textile length thermoplastic fibers, i.e., fibers on the order of ½ to 3 inches long, further advantages can be realized. When heat embossing is applied to such a web in patterns which insure a distance between densified areas smaller than the length of the staple fibers, at least some of the longer staple fibers bridge the distance between adjacent densified regions to provide a further enhanced supporting network.

BRIEF DESCRIPTION OF THE DRAWING

The invention will now be described with reference to the accompanying drawing, in which:

FIG. 1 is a diagrammatic representation in cross section of a preferred form of the invention and showing the same in combination with an additional densified skin;

FIG. 2 is a diagrammatic side elevation view of one form of apparatus for producing the absorbent batt of FIG. 1;

FIG. 3 is a view similar to FIG. 1 but illustrating another preferred form of the invention employing staple length thermoplastic fibers;

FIG. 4 is a diagrammatic side elevation view of one form of apparatus for producing the absorbent batt of FIG. 3;

FIG. 5 is a fragmentary plan view of one face of the batt shown in FIG. 3; and

FIG. 6 is a plan view of the embossing rollers of FIG. 4 for producing the pattern illustrated in FIG. 5.

DETAILED DESCRIPTION OF THE INVENTION

FIG. 1 is a diagrammatic representation of an enlarged cross sectional view of an absorbent batt 10 embodying the principles of the invention. Batt 10 is formed of a substantially homogeneous mixture or blend of TMP fibers 12 and thermoplastic fibers 14 (stippled) intermixed therewith. Both the TMP fibers 12 and thermoplastic fibers 14 are of paper making fiber length, on the order of ¼ inch or less. The thermoplastic fibers 14 may consist of any of a number of low melt plastics such as polyethylene, polypropylene, low melt polyester, polyvinylchloride and polyvinylidene chloride, with polyethylene being the preferred plastic. In any case, the melting temperature of the thermoplastic fibers should be on the order of 30° to 40° F. below the melting point of lignin which, while not fixed, is approximately 275° F. An example of thermoplastic fibers of the present invention are synthetic wood pulp fibers formed of polyethylene that are sold by Crown Zellerbach under the trademark SWP.

Batt 10 comprises predominantly TMP fibers 12, on the order of 75% to 95% of the blend. Concomitantly, the concentration of thermoplastic fibers 14 is in the range of 5% to 25%. The bonding and stabilization of the batt 10 may be carried out at a temperature of about 230° F., or approximately 40°–45° F. below the melting point of the lignin in the TMP fibers 12. Bonding can also be carried out in a compressed state where the density of the batt 10 is about 0.15 gm/cc, although density in the ranges of 0.08 gm/cc and 0.2 gm/cc is acceptable. In this regard, it has been learned that the lower the content of thermoplastic fibers 14, the higher the density should be at bonding.

When batt 10 is heated as set forth above, at least a substantial percentage of the short thermoplastic fibers are melted and the melted fibers form beads or globules 13 that flow to the intersections of TMP fibers 12. Upon cooling and solidification, the globules 13 define thermoplastic fiber bond sites which retain the fibers 14 in a stabilized fiber network. With this arrangement, the interstices between the fibers 14 are maintained to thereby provide the batt with enhanced absorptive capacity. While the present invention contemplates that substantially all of the short thermoplastic fibers may be melted to form beads or globules, some of the thermoplastic fibers may retain at least a portion of their fiber identity, in which case such fibers may fuse to one another and to the fibers 14 to provide further thermoplastic fiber bond sites.

FIG. 2 illustrates diagrammatically a form of apparatus 20 suitable for producing the batt 10. Apparatus 20 thus may comprise a Dual Rotor Webber 22 of well known construction in which thorough mixing of the TMP and short thermoplastic fibers is achieved. The substantially homogeneous mixture of fibers 24 is fed continuously onto an endless screen 26 which may also include vacuum means (not shown) for drawing the mixture against the screen to form the web 28. The web 28 is compressed between rotating rollers 30 and 30, one or both of which is heated to the desired bonding temperature, and which may be adjusted to apply the desired bonding pressure. The batt 10 is thereafter taken up on suitable product rolls PR and stored for future use as needed. Other heating means may be utilized such as the application of heated air.

Depending on the specific requirements of the product application in which the batt 10 is used, the batt 10 may be further stabilized in a number of ways. In one form of the invention, the batt 10 is embossed with line patterns which not only stabilizes the batt but provides a means of distributing liquid through the smaller capillaries created by the embossing. The embossing may be applied by any well known apparatus (not shown) and in any desired patterns, such as illustrated in U.S. Pat. No. 4,154,883.

Another means of enhancing stabilization, while also providing a wicking layer, is illustrated in FIG. 1 of the drawings. In this embodiment, there is shown a second layer 15 comprised of chemical pulp fibers, wherein the fibers are bonded to one another to form a paper-like densified skin (see U.S. Pat. No. 3,017,304) in a known manner (see, for example, U.S. Pat. No. 3,768,118). Embossing of the type described may also be employed in this embodiment of the invention. It will be understood that the chemical pulp fibers may be air laid on screen 26 upstream of the Dual Rotor Webber 22, and that the skin may be formed upstream or downstream of the Dual Rotor Webber.

Referring now to FIG. 3 of the drawings, there is illustrated still another embodiment of the stabilized absorbent batt of the present invention. Here it will be seen that the batt 40 comprises a substantially homogeneous blend of TMP fibers 12 and thermoplastic fibers 42. It is important to note that the thermoplastic fibers 42 here are of staple length, on the order ½ to 3 inches. Embossing is applied to the batt 40 in a pattern so that the distance between grooves or densified areas 44, 44, is less than the length of the staple length fibers 42 such as, for example, the 1 inch spacing shown. It will thus be appreciated that the staple fibers will bridge the distance between adjacent embossed grooves 44 to afford a supporting structure of high stability. It will also be appreciated and understood that short length thermoplastic fibers, such as SWP fibers, may be blended into batt 40 in addition to staple length thermoplastic fibers 42.

In FIG. 4, there is diagrammatically illustrated an apparatus 50 for producing the batt 40. As described in relation to FIG. 2, the apparatus 50 comprises a Dual Rotor Webber 22, or Rando Webber, for mixing the blend of TMP fibers 12 and staple thermoplastic fibers 42. The substantially homogeneous mixture 46 is fed continuously onto an endless screen 26 to form a web 47. The staple fibers 42 are heat and pressure bonded as earlier described (not shown) and the web 47 then passes through embossing means such as 48. Since staple length thermoplastic fibers are drawn and more highly crystalline than the short thermoplastic fibers of the type set forth above, such fibers will maintain their fiber identity upon heating and will bond to one another and to the fibers 14 to stabilize the resulting batt.

An effective embossing pattern for carrying out the invention may be seen in FIG. 5, where the grooves 44 form a modified diamond pattern with maximum distance between adjacent grooves in the direction transverse to the length of the web 47 is about 1 inch. Such a pattern may be formed by a succession of oppositely oriented spiral rolls 52 and 54 in manner well known to the art and is shown in FIG. 6.

The above detailed description of this invention has been given for clarity of understanding only. No unnecessary limitations are to be understood therefrom, as modifications will be obvious to those skilled in the art.

What is claimed is:

1. A stabilized batt comprising: a batt of non-delignified wood pulp fibers, said fibers providing a plurality of fiber intersections throughout said batt; and a minor proportion of at least about five percent (5%) of bonding fibers consisting of thermoplastic fibers substantially evenly distributed throughout said batt and having been rendered tacky by heat to provide bond sites throughout the thickness of said batt, at least some of said bond sites being present at said fiber intersections to retain said non-delignified wood pulp fibers in a fiber network to thereby stabilize said batt.

2. An absorbent batt according to claim 1 in which said thermoplastic fiber bond sites are provided by portions of thermoplastic fibers.

3. An absorbent batt according to claim 2 wherein said thermoplastic fibers are staple length fibers.

4. An absorbent batt according to claim 2 wherein said thermoplastic fibers are synthetic wood pulp fibers.

5. An absorbent batt according to claim 4 wherein at least some of said synthetic wood pulp fibers are melted to form globules.

6. An absorbent batt according to claim 1 in which said web is compressed to a density of from 0.08 gm/cc to 0.2 gm/cc.

7. An absorbent batt according to claim 1 and comprising further heat embossing on a surface thereof to provide locally densified areas.

8. An absorbent batt according to claim 1 in which said non-delignified wood pulp fibers comprise thermo-mechanical wood pulp fibers, said thermo-mechanical wood pulp fibers comprising a majority of the total fibers in said web.

9. An absorbent batt according to claim 8 in which the proportion of thermo-mechanical wood pulp fibers in said web is between 75% and 95%.

10. An absorbent batt according to claim 9 in which said thermoplastic fiber bond sites are provided by thermoplastic fibers that comprise synthetic wood pulp fibers made from a plastic having a melting temperature below 275° F.

11. An absorbent batt according to claim 10 in which said thermoplastic fibers comprise synthetic wood pulp fibers made of a plastic selected from a group consisting of polyethylene, polypropylene, low melt polyester, polyvinyl chloride, and polyvinylidene chloride.

12. An absorbent batt according to claim 11 in which said synthetic wood pulp fibers comprise polypropylene.

13. An absorbent batt according to claim 8 and comprising further a layer of chemical pulp fibers at one surface of said web, said layer having a densified paper-like skin formed on the outer surface thereof.

14. An absorbent batt according to claim 8 in which said thermoplastic fibers comprise staple length fibers made from a plastic having a melting temperature below 275° F.

15. An absorbent batt according to claim 14 in which said staple length fibers are made of a plastic selected from a group consisting of polyethylene, polypropylene, low melt polyester, polyvinyl chloride and polyvinylidene chloride.

16. An absorbent batt according to claim 15 and comprising further heat embossing on a surface of said web, and embossing comprising a pattern of grooves wherein adjacent ones of said grooves are spaced a distance shorter than the length of said staple fibers whereby said staple fibers bridge such adjacent grooves.

17. An absorbent batt according to claim 8 in which said thermoplastic fiber bond sites are provided by a blend of synthetic wood pulp fibers and staple length fibers.

18. The method of stabilizing a batt formed predominantly of non-delignified wood pulp fibers comprising the steps of: uniformly blending a minor amount of thermoplastic fibers with a major amount of non-delignified wood pulp fibers to form a web, and heating said web to a temperature sufficient to bond at least some of said thermoplastic fibers to one another and to at least some of said non-delignified wood pulp fibers at fiber intersections.

19. The method of claim 17 wherein said heating step includes embossing said web to provide capillary passages of reduced size thereby defining a liquid distribution means.

20. The method of claim 17 wherein said blending step is performed by blending synthetic wood pulp fibers with said non-delignified fibers.

21. The method of claim 17 wherein said blending step is performed by blending staple length thermoplastic fibers with said non-delignified fibers.

* * * * *